(12) United States Patent
Nonaka

(10) Patent No.: US 8,962,284 B2
(45) Date of Patent: Feb. 24, 2015

(54) SULFUR-CONTAINING AMINO ACID-PRODUCING BACTERIUM AND METHOD FOR PRODUCING SULFUR-CONTAINING AMINO ACID

(71) Applicant: Ajinomoto Co., Inc., Tokyo (JP)

(72) Inventor: Gen Nonaka, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 13/783,817

(22) Filed: Mar. 4, 2013

(65) Prior Publication Data

US 2013/0164793 A1 Jun. 27, 2013

Related U.S. Application Data

(63) Continuation of application No. PCT/JP2011/070850, filed on Sep. 13, 2011.

(30) Foreign Application Priority Data

Sep. 14, 2010 (JP) .................................. 2010-205019

(51) Int. Cl.
| | |
|---|---|
| C12P 13/12 | (2006.01) |
| C12P 17/16 | (2006.01) |
| C12N 1/21 | (2006.01) |
| C07K 14/245 | (2006.01) |
| C12N 9/10 | (2006.01) |
| C12N 9/04 | (2006.01) |
| C12R 1/19 | (2006.01) |

(52) U.S. Cl.
CPC ................. *C12P 13/12* (2013.01); *C12P 17/16* (2013.01); *C07K 14/245* (2013.01); *C12N 9/1029* (2013.01); *C12N 9/0006* (2013.01); *C12R 1/19* (2013.01)
USPC .... 435/113; 435/120; 435/252.3; 435/252.33

(58) Field of Classification Search
None
See application file for complete search history.

(56) References Cited

U.S. PATENT DOCUMENTS

| | | | |
|---|---|---|---|
| 5,856,148 | A | 1/1999 | Burlingame |
| 5,972,663 | A | 10/1999 | Winterhalter et al. |
| 6,218,168 | B1 | 4/2001 | Leinfelder et al. |
| 7,148,047 | B2 | 12/2006 | Takagi et al. |
| 7,611,873 | B1 | 11/2009 | Usuda et al. |
| 8,008,048 | B2 | 8/2011 | Nonaka et al. |
| 8,114,649 | B2 | 2/2012 | Takagi et al. |
| 8,206,954 | B2 | 6/2012 | Takikawa et al. |
| 8,278,075 | B2 | 10/2012 | Nonaka et al. |
| 8,293,506 | B2 | 10/2012 | Nonaka et al. |
| 2003/0077766 | A1 | 4/2003 | Takagi et al. |
| 2005/0009162 | A1 | 1/2005 | Maier et al. |
| 2005/0112731 | A1 | 5/2005 | Kashiwagi et al. |
| 2005/0221453 | A1 | 10/2005 | Takagi et al. |
| 2008/0076163 | A1 | 3/2008 | Takagi et al. |
| 2009/0226982 | A1 | 9/2009 | Takagi et al. |
| 2009/0226984 | A1 | 9/2009 | Nonaka et al. |
| 2010/0093045 | A1 | 4/2010 | Takagi et al. |
| 2010/0209977 | A1 | 8/2010 | Takumi et al. |
| 2010/0233765 | A1 | 9/2010 | Nonaka et al. |
| 2011/0177566 | A1 | 7/2011 | Savrasova et al. |
| 2012/0252076 | A1 | 10/2012 | Yamazaki et al. |
| 2012/0288902 | A1 | 11/2012 | Nonaka et al. |

FOREIGN PATENT DOCUMENTS

| | | |
|---|---|---|
| EP | 1528108 | 5/2005 |
| JP | 11-155571 | 6/1999 |
| JP | 2002-233384 | 8/2002 |
| JP | 2003-169668 | 6/2003 |
| JP | 2005-245311 | 9/2005 |
| JP | 2005-287333 | 10/2005 |
| WO | WO01/27307 | 4/2001 |
| WO | WO2012/036151 | 3/2012 |

OTHER PUBLICATIONS

Wahl et al., Molecular hybridization of immobilized nucleic acids, Methods Enz., 1987, 152, 399-407.*
Gristwood et al., PigS and PigP regulate prodigiosin biosynthesis in *Serratia* via differential control of divergent operons, which include predicted transporters of sulfur-containing molecules, J. Bacteriol., Dec. 2010, 193, 1076-85.*
Wang et al., Transcriptomic response of *Escherichia coli* O157:H7 to oxidative stress, Appl. Environ. Microbiol., 2009, 75, 6110-23.*
Arfin, S. M., et al., "Global Gene Expression Profiling in *Escherichia coli* K12," J. Biol. Chem. 2000;275(38):29672-29684.
Arnold, C. N., et al., "Global Analysis of *Escherichia coli* Gene Expression during the Acetate-Induced Acid Tolerance Response," J. Bacteriol. 2001;183(7):2178-2186.

(Continued)

*Primary Examiner* — Rebecca Prouty
*Assistant Examiner* — Todd M Epstein
(74) *Attorney, Agent, or Firm* — Shelly Guest Cermak; Cermak Nakajima & McGowan LLP

(57) ABSTRACT

A novel technique for improving the production by bacteria of amino acids that contain sulfur has been developed, and thereby a sulfur-containing amino acid-producing bacterium, and a method for producing a compound such as a sulfur-containing amino acid are provided. A sulfur-containing amino acid, a related substance thereof, or a mixture of these can be produced by culturing a bacterium belonging to the family Enterobacteriaceae, which has a sulfur-containing amino acid-producing ability and has been modified so that the activity of the protein encoded by the yeeE gene, for example, the protein of the following (A) or (B), is increased in a medium, and collecting a sulfur-containing amino acid, a related substance thereof, or a mixture of them from the medium: (A) a protein having the amino acid sequence of SEQ ID NO: 14, (B) a protein having the amino acid sequence of SEQ ID NO: 14 but which includes one or several amino acid substitutions, deletions, insertions, or additions, and when the intracellular activity of this protein is increased, the ability of the bacterium to produce a sulfur-containing amino acid is improved.

9 Claims, 1 Drawing Sheet

(56) References Cited

OTHER PUBLICATIONS

BioCyc Home Page, *Escherichia coli* K12 substr. MG1655 Gene: *yeeE* [searched on Jul. 13, 2010], Internet URL <http://biocyc.org/ECOLI/NEW-IMAGE?type=GENE&object=EG11895.

Daβler, T., et al., "Identification of a major facilitator protein from *Escherichia coli* involved in efflux of metabolites of the cysteine pathway," Mol. Microbiol. 2000;36(5):1101-1112.

Kabir, Md. S., et al., "Cell lysis directed by $\sigma^E$ in early stationary phase and effect of induction of the *rpoE* gene on global gene expression in *Escherichia coli*," Microbiol. 2005;151:2721-2735.

Ren, D., et al., "Differential Gene Expression for Investigation of *Escherichia coli* Biofilm Inhibition by Plant Extract Ursolic Acid," Appl. Environ. Microbiol. 2005;71(7):4022-4034.

International Preliminary Report on Patentability for PCT Patent App. No. PCT/JP2011/070850 (Mar. 28, 2013).

Database DDBJ/EMBL/GenBank [online], Accession No. AB453015, Apr. 3, 2009.

Database DDBJ/EMBL/GenBank [online]. Accession No. P33015, Aug. 10, 2010.

Helbig, K., et al., "Cadmium Toxicity in Glutathione Mutants of *Escherichia coli*," J. Bacteriol. 2008;190(15):5439-5454.

Nobre, L.S., et al., "Exploring the antimicrobial action of a carbon monoxide-releasing compound through whole-genome transcription profiling of *Escherichia coli*," Microbiol. 2009;155:813-824.

White-Ziegler, C. A., et al., "Human Body Temperature (37° C.) Increases the Expression of Iron, Carbohydrate, and Amino Acid Utilization Genes in *Escherichia coli* K-12," J. Bacteriol. 2007;189(15):5429-5440.

Yamamoto, K., et al., "Transcriptional Response of *Escherichia coli* to External Zinc," J. Bacteriol. 2005;187(18):6333-6340.

International Search Report for PCT Patent App. No. PCT/JP2011/070850 (Dec. 13, 2011).

Supplementary European Search Report for EP Patent App. No. 11825153.7 (Jan. 21, 2014).

\* cited by examiner

```
Pnlp0.  AAAACGTGAGGAAATACCTGGATTTTTCCTGGTTATTTTGCCGCAGGTCAGCGTATCGTG
Pnlp8.  AAAACGTGAGGAAATACCTGGATTTTTCCTGGTTATTTTGCCGCAGGTCAGCGTATAATG
                                     P2(-35)                  P2(-10)

Pnlp0.  AACATCTTTTCCAGTGTTCAGTAGGGTGCCTTGCACGGTAATTATGTCACTGGTTATTAA
Pnlp8.  AAGATCTTTTCCAGTGTTGACAAGGGTGCCTTGCACGGTTATAATGTCACTGGTTATTAA
                       P1(-35)                 P1(-10)

Pnlp0.  CCAATTTTTCCTGGGGGATAAATG······
Pnlp8.  CCAATTTTTCCTGGGGGATAAATG······
                                Met······
```

SULFUR-CONTAINING AMINO ACID-PRODUCING BACTERIUM AND METHOD FOR PRODUCING SULFUR-CONTAINING AMINO ACID

This application is a Continuation of, and claims priority under 35 U.S.C. §120 to, International Application No. PCT/JP2011/070850, filed Sep. 13, 2011, and claims priority therethrough under 35 U.S.C. §119 to Japanese Patent Application No. 2010-205019, filed Sep. 14, 2010, the entireties of which are incorporated by reference herein. Also, the Sequence Listing filed electronically herewith is hereby incorporated by reference (File name: 2013-03-04T_US-493_Seq_List; File size: 13 KB; Date recorded: Mar. 4, 2013).

BACKGROUND OF THE INVENTION

1. Field of the Invention

The present invention relates to a method for producing a sulfur-containing amino acid such as L-cysteine, or a related substance thereof. Specifically, the present invention relates to a bacterium suitable for producing a sulfur-containing amino acid or a related substance thereof, and a method for producing a sulfur-containing amino acid or a related substance thereof utilizing such a bacterium. Sulfur-containing amino acids and related substances thereof are used in the fields of drugs, cosmetics, and foods.

2. Brief Description of the Related Art

L-cysteine is conventionally obtained by extraction from keratin-containing substances such as hair, horns, and feathers, or by conversion of the precursor DL-2-aminothiazoline-4-carboxylic acid with a microbial enzyme. L-cysteine has also been planned for production on a large scale by the immobilized enzyme method utilizing a novel enzyme. Furthermore, it has also been attempted to produce L-cysteine by fermentation utilizing a microorganism.

Microorganisms that are able to produce L-cysteine are known, for example, a coryneform bacterium with increased intracellular serine acetyltransferase activity (Japanese Patent Laid-open (Kokai) No. 2002-233384). Increasing L-cysteine-producing ability by incorporating a mutant serine acetyltransferase which is attenuated to L-cysteine feedback inhibition has also been reported (Japanese Patent Laid-open (Kokai) No. 11-155571, U.S. Patent Published Application No. 20050112731, and U.S. Pat. No. 6,218,168).

Furthermore, microorganisms which are able to produce an enhanced amount of L-cysteine by suppressing the L-cysteine decomposition system include coryneform bacteria, or *Escherichia* bacteria in which the activity of cystathionine-β-lyase (Japanese Patent Laid-open (Kokai) No. 11-155571), tryptophanase (Japanese Patent Laid-open (Kokai) No. 2003-169668), or O-acetylserine sulfhydrylase B (Japanese Patent Laid-open (Kokai) No. 2005-245311) is attenuated or deleted.

Furthermore, the ydeD gene encoding the YdeD protein is known to participate in secretion of the metabolic products of the cysteine pathway (Dassler et al., Mol. Microbiol., 36, 1101-1112 (2000)). Other known methods of enhancing L-cysteine-producing ability include increasing the expression of the mar-locus, emr-locus, acr-locus, cmr-locus, mex-gene, bmr-gene, or qacA-gene (U.S. Pat. No. 5,972,663), or emrAB, emrKY, yojIH, acrEF, bcr, or cusA gene (Japanese Patent Laid-open (Kokai) No. 2005-287333). These loci/genes encode a protein suitable for excreting a cytotoxic substance.

Another known L-cysteine-producing bacterium is *Escherichia coli* in which the activity of the positive transcriptional control factor of the cysteine regulon encoded by the cysB gene is increased (International Patent Publication WO01/27307).

Furthermore, a mutant serA coding for 3-phosphoglycerate dehydrogenase with attenuated feedback inhibition by serine, and the use thereof for L-cysteine production by *Escherichia coli* has been suggested (U.S. Pat. No. 5,856,148 and U.S. Patent Published Application No. 20050009162).

Methionine is industrially produced mainly by chemical synthesis as a mixture of D- and L-isomers. When the L-isomer is required, it can be produced by acetylating the D- and L-isomers to convert them into N-acetyl-DL-methionine, and enzymatically deacetylating only the L-isomer. Production of L-methionine by fermentation has also been attempted using a microorganism. As L-methionine-producing bacteria, *Escherichia coli* bacteria have been reported that are deficient in the repressor of the L-methionine biosynthesis system, and which have enhanced intracellular homoserine transsuccinylase activity, attenuated intracellular S-adenosylmethionine synthetase activity, L-threonine auxotrophy, enhanced intracellular cystathionine γ-synthase activity, and enhanced intracellular aspartokinase-homoserine dehydrogenase II activity (U.S. Pat. No. 7,611,873), and so forth.

The yeeE gene is registered in the database EcoCyc (BioCyc Home Page, *Escherichia coli* K-12 substr. MG1655 Gene: yeeE [searched on Jul. 13, 2010], Internet URL biocyc.org/ECOLI/NEW-IMAGE?type=GENE&object=EG11895) as a gene coding for a putative transport system permease protein. Furthermore, according to an analysis using the membrane protein prediction program SOSUI (bp.nuap-.nagoya-u.ac.jp/sosui/sosui_submit.html), YeeE is predicted to be a nine-transmembrane protein. Therefore, YeeE is presumed to be a type of transporter, but the actual functions are unknown. Furthermore, the relation of YeeE to production of sulfur-containing amino acids has not been reported.

Furthermore, the yeeE gene has been reported to be up-regulated by cadmium (Kerstin et al., J. Bacteriol., Aug. 2008, 190:5439-5454), by zinc (Kaneyoshi et al., J. Bacteriol., Sep. 2005, 187:6333-6340), by CORM-2, which is a CO-discharging agent (Ligia S., Nobre et al., Microbiology, Mar. 2009, 155:813-824), at an early stage of the stationary phase in an RpoE-dependent manner (Md. Shahinur Kabir et at, Microbiology, August 2005, 151:2721-2735), and at a temperature of 37° C., which is the human body temperature (Christine A. et at, J. Bacteriol., Aug. 2007, 189:5429-5440). The yeeE gene has also been reported to be down-regulated by acetic acid (Carrie N. Arnold et al., J. Bacteriol., Apr. 2001, 183: 2178-2186), by ursolic acid (Dacheng Ren et at, Appl. Envir. Microbiot, Jul. 2005, 71:4022-4034), and in the IHF(−) strain (Stuart M. Arfin et al., J. Biol. Chem., Sep. 2000, 275:29672). However, in the literature, the yeeE gene is only mentioned as one of many genes that show change of expression in microarray experiments, and the relation of this gene with production of sulfur-containing amino acids has not been suggested or reported.

SUMMARY OF THE INVENTION

One aspect of the present invention is to develop a novel technique for improving the ability of a bacterium to produce a sulfur-containing amino acid, and thereby provide a sulfur-containing amino acid-producing bacterium, and a method for producing a sulfur-containing amino acid, a related substance thereof, or a mixture of them by using such a bacterium.

It has been found that the ability of a bacterium to produce a sulfur-containing amino acid can be enhanced by modifying the bacterium so that the activity of the protein encoded by the yeeE gene is increased.

It is an aspect of the present invention to provide a bacterium belonging to the family Enterobacteriaceae, which has a sulfur-containing amino acid-producing ability and is modified so that the activity of the protein encoded by the yeeE gene is increased.

It is a further aspect of the present invention to provide the above described bacterium, wherein the activity of the protein is increased by a method selected from the group consisting of: a) increasing the expression amount of the yeeE gene, b) increasing the translation amount of the yeeE gene, and c) combinations thereof.

It is a further aspect of the present invention to provide the above described bacterium, wherein the expression amount of the yeeE gene is increased by a method selected from the group consisting of: a) increasing the copy number of the yeeE gene, b) modifying an expression control sequence of the yeeE gene, and c) combinations thereof.

It is a further aspect of the present invention to provide the above described bacterium, wherein the protein is selected from the group consisting of: a) a protein comprising the amino acid sequence of SEQ ID NO: 14, and b) a protein comprising the amino acid sequence of SEQ ID NO: 14, but which includes one or more amino acid substitutions, deletions, insertions, or additions, and wherein the increase in said protein activity improves the ability of said bacterium to produce a sulfur-containing amino acid.

It is a further aspect of the present invention to provide the above described bacterium, wherein the yeeE gene comprises a DNA selected from the group consisting of: a) a DNA comprising the nucleotide sequence of SEQ ID NO: 13, and b) a DNA which is able to hybridize to a sequence complementary to the nucleotide sequence of SEQ ID NO: 13, or a probe which is prepared from the nucleotide sequence, under stringent conditions, and wherein said DNA encodes a protein which improves the ability of said bacterium to produce a sulfur-containing amino acid when the activity of said protein is increased in said bacterium.

It is a further aspect of the present invention to provide the above described bacterium, which has at least one of the following characteristics: a) increased serine acetyltransferase activity, b) increased expression of the ydeD gene, c) increased 3-phosphoglycerate dehydrogenase activity.

It is a further aspect of the present invention to provide the above described bacterium, which is an *Escherichia* bacterium.

It is a further aspect of the present invention to provide the above described bacterium, which is *Escherichia coli*.

It is a further aspect of the present invention to provide the above described bacterium, which is a *Pantoea* bacterium.

It is a further aspect of the present invention to provide the above described bacterium, which is *Pantoea ananatis*.

It is a further aspect of the present invention to provide a method for producing a sulfur-containing amino acid, a related substance thereof, or a mixture thereof, which comprises culturing the aforementioned bacterium in a medium, and collecting a sulfur-containing amino acid, a related substance thereof, or a mixture thereof from the medium.

It is a further aspect of the present invention to provide the above described method, wherein the sulfur-containing amino acid is L-cysteine.

It is a further aspect of the present invention to provide the above described method, wherein the sulfur-containing amino acid is L-cysteine, and the related substance thereof is cystine or a thiazolidine derivative.

According to the present invention, the ability of a bacterium to produce a sulfur-containing amino acid can be improved. Furthermore, according to the present invention, a sulfur-containing amino acid, a related substance thereof, or a mixture thereof can be efficiently produced.

BRIEF DESCRIPTION OF THE DRAWING

FIG. 1 shows the sequences of the ligation sites of the wild-type nlpD promoter (Pnlp, SEQ ID NO: 15) and the variant nlpD promoter (Pnlp8, SEQ ID NO: 16) with the yeaS gene.

DESCRIPTION OF THE PREFERRED EMBODIMENTS

<1> Bacterium

The bacterium in accordance with the presently described subject matter can belong to the family Enterobacteriaceae, can have the ability to produce a sulfur-containing amino acid, and can be modified so that the activity of the protein encoded by the yeeE gene is increased.

Examples of the sulfur-containing amino acid can include L-cysteine and L-methionine. The bacterium can have an ability to produce both L-cysteine and L-methionine.

The sulfur-containing amino acid can be in a free form, a salt thereof, or a mixture of these. Examples of the salt can include, for example, sulfate, hydrochloride, carbonate, ammonium salt, sodium salt, and potassium salt.

The ability of a bacterium to produce a sulfur-containing amino acid can mean the ability to produce and accumulate a sulfur-containing amino acid, a related substance thereof, or a mixture of these in a medium or the bacterial cells in such an amount that it can be collected from the medium or the bacterial cells when the bacterium is cultured in the medium. A bacterium that is able to produce a sulfur-containing amino acid can also mean a bacterium that can produce and accumulate a larger amount of the sulfur-containing amino acid, a related substance thereof, or a mixture of these in a medium compared with a wild-type strain, an unmodified strain, or a parent strain. It can also mean the sulfur-containing amino acid, a related substance thereof, or a mixture of these can be produced and accumulated in a medium in an amount of 0.05 g/L or more, 0.1 g/L or more, or even 0.2 g/L or more.

When the sulfur-containing amino acid is L-cysteine, a portion of L-cysteine produced by a bacterium can be converted into L-cystine in the medium by formation of a disulfide bond. Furthermore, S-sulfocysteine can be generated by the reaction between L-cysteine and thiosulfate contained in the medium (Szczepkowski T. W., Nature, vol. 182 (1958)). L-cysteine that is generated in bacterial cells can be condensed with a ketone or an aldehyde, for example pyruvic acid, which is present in the cells, so that a thiazolidine derivative is produced via a hemithioketal as an intermediate (refer to Japanese Patent No. 2992010). The thiazolidine derivative and hemithioketal can exist as an equilibrated mixture. Furthermore, L-cysteine can be a starting material in the biosyntheses of γ-glutamylcysteine, glutathione, cystathionine, homocysteine, and so forth. Therefore, by using a bacterium having an ability to produce any of these compounds in addition to an ability to produce L-cysteine, the corresponding compound can be produced. The L-cysteine-producing ability is not limited to an ability to accumulate only L-cysteine in a medium or cells, but includes an ability to accumulate L-cysteine, L-cystine, derivatives thereof described above, for example, S-sulfocysteine, a thiazolidine derivative, or a hemithioketal, other compounds produced via L-cysteine as described herein, for example, γ-glutamylcysteine, glutathione, cystathionine, or homocysteine, or a mixture thereof in the medium. L-cystine, L-cysteine derivatives as described above, and other compounds produced via L-cysteine as mentioned above can be collectively referred to as related substances of L-cysteine.

L-methionine is a sulfur-containing amino acid biosynthesized by using L-cysteine as one of the starting materials. Furthermore, L-methionine can be used as a starting material of the biosynthesis of S-adenosylmethionine or the like. Therefore, when the sulfur-containing amino acid is L-methionine, S-adenosylmethionine or the like can be produced by using a bacterium having an ability to produce S-adenosylmethionine or the like in addition to an ability to produce L-methionine. The bacterium as described herein is not limited to a bacterium which can accumulate only L-methionine in a medium or cells, but can also accumulate other compounds, or mixtures of such compounds, which are produced via L-methionine, for example, S-adenosylmethionine. Compounds that can be produced via L-methionine can also be referred to as related substances of L-methionine.

The ability of a bacterium to produce sulfur-containing amino acids can mean an ability to accumulate L-cysteine, a related substance of L-cysteine, L-methionine, a related substance of L-methionine, or a mixture of these in a medium. Furthermore, the related substances of L-cysteine and the related substances of L-methionine can also be collectively referred to as related substances of sulfur-containing amino acids.

The bacterium in accordance with the presently described subject matter can be a bacterium which inherently produces sulfur-containing amino acids, or it can be a bacterium which is modified by mutagenesis or a recombinant DNA technique so that it acquires the ability to produce sulfur-containing amino acids.

The bacterium is not particularly limited so long as it belongs to the family Enterobacteriaceae, such as those of the genera *Escherichia, Enterobacter, Pantoea, Klebsiella, Serratia, Erwinia, Salmonella*, and *Morganella*, and has a sulfur-containing amino acid-producing ability. Specifically, those classified into the family Enterobacteriaceae according to the taxonomy used in the NCBI (National Center for Biotechnology Information) database www.ncbi.nlm.nih.gov/Taxonomy/Browser/wwwtax.cgi?id=91347) can be used. Parent strains of the family Enterobacteriaceae that can be used for modification include a bacterium of the genus *Escherichia, Enterobacter, Pantoea, Erwinia, Enterobacter*, or *Klebsiella*.

Although the *Escherichia* bacteria are not particularly limited, specifically, those described in the work of Neidhardt et al. (Backmann B. J., 1996, Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.) can be used. Among them, for example, *Escherichia coli* can be exemplified. Specific examples of *Escherichia coli* include *Escherichia coli* W3110 (ATCC 27325), *Escherichia coli* MG1655 (ATCC 47076), and so forth, which are derived from the prototype wild-type strain K12.

These strains are available from, for example, the American Type Culture Collection (Address: P.O. Box 1549, 10801 University Boulevard, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection.

Examples of the *Enterobacter* bacteria include, for example, *Enterobacter agglomerans* and *Enterobacter aerogenes*. An example of a typical strain of the genus *Enterobacter* includes *Enterobacter agglomerans* ATCC 12287. Also, specifically, the strains exemplified in European Patent Publication No. 952221 can be used.

Examples of the *Pantoea* bacteria include, for example, *Pantoea ananatis, Pantoea stewartii, Pantoea agglomerans*, and *Pantoea citrea*.

Specific examples of *Pantoea ananatis* include the *Pantoea ananatis* AJ13355 strain and SC17 strain. The SC17 strain was selected as a low phlegm-producing mutant strain from the AJ13355 strain (FERM BP-6614) isolated from soil in Iwata-shi, Shizuoka-ken, Japan as a strain that can proliferate in a low pH medium containing L-glutamic acid and a carbon source (U.S. Pat. No. 6,596,517). The *Pantoea ananatis* AJ13355 strain was deposited at the National Institute of Bioscience and Human-Technology, Agency of Industrial Science and Technology, Ministry of International Trade and Industry (currently, the National Institute of Advanced Industrial Science and Technology, International Patent Organism Depositary, Address: Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. The *Pantoea ananatis* SC17 strain was deposited at the National Institute of Advanced Industrial Science and Technology, International Patent Organism Depositary (Address: Tsukuba Central 6, 1-1, Higashi 1-Chome, Tsukuba-shi, Ibaraki-ken, 305-8566, Japan) on Feb. 4, 2009 and assigned an accession number of FERM BP-11091. The *Pantoea ananatis* AJ13355 strain was identified as *Enterobacter agglomerans* when it was first isolated, and deposited as the *Enterobacter agglomerans* AJ13355 strain. However, it was recently reclassified into *Pantoea ananatis* on the basis of nucleotide sequence analysis of 16S rRNA and so forth.

Examples of the *Erwinia* bacteria include *Erwinia amylovora* and *Erwinia carotovora*, and examples of the *Klebsiella* bacteria include *Klebsiella planticola*.

In particular, *Pantoea* bacteria, *Erwinia* bacteria, and *Enterobacter* bacteria are classified as γ-proteobacteria, and they are taxonomically very close to one another (J. Gen. Appl. Microbiol., 1997, 43, 355-361; International Journal of Systematic Bacteriology, Oct. 1997, pp. 1061-1067). Therefore, some bacteria belonging to the genus *Enterobacter* were reclassified into *Pantoea agglomerans, Pantoea dispersa*, or the like, on the basis of DNA-DNA hybridization experiments etc. (International Journal of Systematic Bacteriology, Jul. 1989, 39(3), pp. 337-345). For example, some strains of *Enterobacter agglomerans* were reclassified into *Pantoea agglomerans, Pantoea ananatis,* or *Pantoea stewartii* on the basis of nucleotide sequence analysis of 16S rRNA etc. Furthermore, some bacteria belonging to the genus *Erwinia* were reclassified into *Pantoea ananas* or *Pantoea stewartii* (refer to International Journal of Systematic Bacteriology, Jan. 1993; 43(1), pp. 162-173). A bacterium belonging to any of the genera *Enterobacter, Pantoea, Erwinia*, and the like can be used so long as it is a bacterium classified into the family Enterobacteriaceae.

Hereinafter, methods for imparting the ability to produce a sulfur-containing amino acid to a bacterium belonging to the family Enterobacteriaceae or methods for enhancing the ability to produce a sulfur-containing amino acid will be described.

To impart the ability to produce a sulfur-containing amino acid to a bacterium, methods conventionally employed in the breeding of coryneform bacteria, *Escherichia* bacteria, or the like can be used. Such methods include acquiring an auxotrophic mutant strain, an analogue-resistant strain, or a metabolic regulation mutant strain, constructing a recombinant strain in which a sulfur-containing amino acid biosynthesis enzyme is overexpressed, and so forth (see "Amino Acid Fermentation", Gakkai Shuppan Center (Ltd.), 1st Edition, published May 30, 1986, pp. 77-100). In the breeding of sulfur-containing amino acid-producing bacteria, the properties such as auxotrophy, analogue resistance, and/or metabolic regulation mutation can be imparted alone or in combinations of two, or three, or more. Also, the expression of a sulfur-containing amino acid biosynthesis enzyme(s) can be enhanced alone or in combinations of two, or three, or more. Furthermore, imparting the properties such as auxotrophy, analogue resistance, and metabolic regulation mutation can be combined with enhancing the biosynthesis enzyme(s).

An auxotrophic mutant strain, sulfur-containing amino acid analogue resistant strain, or metabolic regulation mutant strain, which is able to produce a sulfur-containing amino acid, can be obtained by subjecting a parent strain, an unmodified strain, or a wild-type strain to conventional mutagenesis, such as exposure to X-rays or UV irradiation or a treatment with a mutagen such as N-methyl-N'-nitro-N-nitrosoguanidine (NTG) or ethyl methanesulfonate (EMS), and then selecting a strain which exhibits autotrophy, analogue resistance, or a metabolic regulation mutation, and which is able to produce a sulfur-containing amino acid from the obtained mutant strains.

Methods for imparting the ability to produce a sulfur-containing amino acid to a bacterium belonging to the family Enterobacteriaceae or methods for enhancing such ability, and bacteria which are able to produce a sulfur-containing amino acid will be specifically exemplified below.

Impartation or Enhancement of L-Cysteine-Producing Ability and L-Cysteine-Producing Bacteria L-cysteine-producing ability of a bacterium can be improved by enhancing the activity of an enzyme of the L-cysteine biosynthesis pathway or an enzyme involved in generation of a substrate compound in that pathway such as L-serine, for example, 3-phosphoglycerate dehydrogenase, serine acetyltransferase, or the like. Because 3-phosphoglycerate dehydrogenase can be the object of feedback inhibition by serine, the activity of this enzyme can be enhanced by mutating the serA gene so that the feedback inhibition is attenuated or eliminated, and incorporating the mutant serA gene into the bacterium. Also, because serine acetyltransferase can be the object of feedback inhibition by L-cysteine, the activity of this enzyme can be enhanced by mutating the cysE gene so that the feedback inhibition is attenuated or eliminated, and incorporating the mutant cysE gene into a bacterium.

L-cysteine-producing ability can also be enhanced by enhancing the expression of the ydeD gene coding for the YdeD protein (Dabler et al., Mol. Microbiol., 36, 1101-1112 (2000)), the yfiK gene coding for the YfiK protein (Japanese Patent Laid-open (Kokai) No. 2004-49237), or the yeaS gene coding for the YeaS protein (European Patent Laid-open No. 1016710).

The L-cysteine-producing bacterium can also be modified to have at least one of the following characteristics as compared to a non-modified bacterium:

i. increased serine acetyltransferase activity,
ii. increased expression of the ydeD gene, and
iii. increased 3-phosphoglycerate dehydrogenase activity.

Furthermore, L-cysteine-producing ability can also be improved by enhancing the activity of the sulfate/thiosulfate transport system. The proteins of the sulfate/thiosulfate transport system are encoded by the cysPTWAM gene cluster (Japanese Patent Laid-open (Kokai) No. 2005-137369, European Patent No. 1528108).

Specific examples of L-cysteine-producing bacteria include, but are not limited to, strains belonging to the genus *Escherichia* such as *E. coli* JM15 strains transformed with multiple kinds of cysE alleles encoding serine acetyltransferase (SAT) resistant to feedback inhibition (U.S. Pat. No. 6,218,168), *E. coli* W3110 strain in which a gene encoding a protein suitable for excreting a cytotoxic substance is overexpressed (U.S. Pat. No. 5,972,663), *E. coli* in which cysteine desulfhydrase activity is decreased (Japanese Patent Laid-open (Kokai) No. 11-155571), *E. coli* W3110 strain in which the activity of the positive transcriptional control factor of the cysteine regulon encoded by the cysB gene is increased (WO01/27307), *E. coli* having the plasmid pACYC-DES (Japanese Patent Laid-open (Kokai) No. 2005-137369; U.S. Patent Published Application No. 20050124049(A1); European Patent Laid-open No. 1528108(A1)) containing the ydeD gene, a mutant cysE gene, and a mutant serA5 gene, and so forth. pACYC-DES is obtained by inserting the above three genes into the plasmid pACYC184, and the expression of each of the genes is controlled by the PompA promoter.

As proteins having the cysteine desulfhydrase activity of *Escherichia coli,* cystathionine-β-lyase (metC product, Japanese Patent Laid-open No. 11-155571, Chandra et al., Biochemistry, 21 (1982) 3064-3069), tryptophanase (tnaA product, Japanese Patent Laid-open (Kokai) No. 2003-169668, Austin Newton et at, J. Biol. Chem., 240 (1965) 1211-1218)), O-acetylserine sulfhydrylase B (cysM gene product, Japanese Patent Laid-open (Kokai) No. 2005-245311), and the malY gene product (Japanese Patent Laid-open (Kokai) No. 2005-245311) are known. By decreasing the activities of these proteins, L-cysteine-producing ability can be improved.

The L-cysteine-producing bacterium can have a mutant SAT which is resistant to feedback inhibition. Examples of mutant SATs which are resistant to feedback inhibition and derived from *Escherichia coli* include SAT in which the methionine residue at position 256 is replaced with glutamate residue (Japanese Patent Laid-open (Kokai) No. 11-155571), SAT in which the methionine residue at position 256 is replaced with isoleucine residue (Denk, D. and Boeck, A., J. General Microbiol., 133, 515-525 (1987)), SAT having a mutation in the region from the amino acid residue at position 97 to the amino acid residue at position 273, or deletion of the C-terminus region from the amino acid residue at position 227 (International Patent Publication WO97/15673, U.S. Pat. No. 6,218,168), SAT in which the amino acid sequence corresponding to positions 89 to 96 of wild-type SAT contains one or several mutations and which is desensitized to feedback inhibition by L-cysteine (U.S. Patent Published Application No. 20050112731(A1)), SAT in which the Val residue and the Asp residue at positions 95 and 96 are replaced with Arg residue and Pro residue, respectively (name of the mutant gene: cysE5, WO2005/007841), the mutation in which the threonine residue at position 167 is replaced with an alanine residue (U.S. Pat. No. 6,218,168, U.S. Patent Published Application No. 20050112731(A1)), and so forth.

The SAT gene is not limited to the gene of *Escherichia coli,* and any gene coding for a protein having the SAT activity can be used. For example, an SAT isozyme of *Arabidopsis* thaliana desensitized to feedback inhibition by L-cysteine is known, and the gene encoding this SAT isozyme can also be used (FEMS Microbiol. Lett., 179, 453-459 (1999)).

By introducing a gene encoding SAT, in particular, a gene encoding a mutant SAT resistant to feedback inhibition, into a bacterium and expressing it, L-cysteine-producing ability can be imparted or enhanced.

Furthermore, by increasing the copy number of a gene coding for a protein such as SAT, the activity of such a protein can be increased.

An ability to produce any compounds biosynthesized from L-cysteine as a starting material, such as γ-glutamylcysteine, glutathione, cystathionine, and homocysteine, can also be imparted or enhanced by enhancing the activity of an enzyme of the biosynthesis pathway of an objective compound, or by reducing the activity of an enzyme of a pathway branching away from the biosynthesis pathway of the objective compound or an enzyme that decomposes the objective compound.

For example, γ-glutamylcysteine-producing ability can be enhanced by enhancing the γ-glutamylcysteine synthetase activity and/or by reducing the glutathione synthetase activity. Also, glutathione-producing ability can be imparted or enhanced by enhancing the γ-glutamylcysteine synthetase activity and/or the glutathione synthetase activity. Furthermore, the ability to produce γ-glutamylcysteine or glutathione can also be enhanced by using a mutant γ-glutamylcysteine synthetase resistant to feedback inhibition by glutathione. Production of glutathione is described in detail in the overview of Li et al. (Yin Li, Gongyuan Wei, Jian Chen, Appl. Microbiol. Biotechnol., 66:233-242 (2004)).

Because cystathionine and homocysteine are intermediates of the L-methionine biosynthesis pathway, it can be effective to partially use the methods for enhancing L-methionine-producing ability described below for enhancing abilities to produce these substances. As specific methods for enhancing cystathionine-producing ability, a method using a methionine-auxotrophic mutant strain (Japanese Patent Application No. 2003-010654) and a method adding cysteine (or raw material for biosynthesis thereof) and/or homoserine (or raw material for biosynthesis thereof) to a fermentation medium (Japanese Patent Laid-open (Kokai) No. 2005-168422) have been reported. Because homocysteine is produced by using cystathionine as a precursor, the aforementioned methods for enhancing cystathionine-producing ability are also effective for enhancing homocysteine-producing ability.

Impartation or Enhancement of L-Methionine-Producing Ability and L-Methionine-Producing Bacteria L-methionine-producing ability can be imparted or enhanced by imparting L-threonine auxotrophy or norleucine resistance to a bacterium (Japanese Patent Laid-open (Kokai) No. 2000-139471). In E. coli, the genes of the enzymes involved in the biosynthesis of L-threonine exist as the threonine operon (thrABC), and an L-threonine auxotrophic strain that has lost the biosynthesis ability for L-homoserine and the following compounds can be obtained by, for example, deleting the thrBC moiety. In a norleucine resistant strain, the S-adenosylmethionine synthetase activity is attenuated, and L-methionine-producing ability is imparted or enhanced. In E. coli, S-adenosylmethionine synthetase is encoded by the metK gene. L-methionine-producing ability can also be imparted or enhanced by deleting the methionine repressor or by enhancing the activity of an enzyme involved in the L-methionine biosynthesis, such as homoserine transsuccinylase, cystathionine γ-synthase, and aspartokinase-homoserine dehydrogenase II (Japanese Patent Laid-open (Kokai) No. 2000-139471). In E. coli, the methionine repressor is encoded by the metJ gene, homoserine transsuccinylase is encoded by the metA gene, cystathionine γ-synthase is encoded by the metB gene, and aspartokinase-homoserine dehydrogenase II is encoded by the metL gene. Furthermore, by using a mutant homoserine transsuccinylase resistant to feedback inhibition by methionine, L-methionine-producing ability can also be imparted or enhanced (Japanese Patent Laid-open (Kokai) No. 2000-139471, U.S. Patent Published Application No. 20090029424). Because L-methionine is biosynthesized via L-cysteine as an intermediate, L-methionine-producing ability can also be improved by improving L-cysteine-producing ability (Japanese Patent Laid-open (Kokai) No. 2000-139471, U.S. Patent Published Application No. 20080311632). Therefore, for imparting or enhancing L-methionine-producing ability, the aforementioned methods for imparting or enhancing L-cysteine-producing ability can also be effective.

Specific examples of L-methionine-producing bacteria, and parent strains which can be modified to construct such bacteria, include E. coli strains such as AJ11539 (NRRL B-12399), AJ11540 (NRRL B-12400), AJ11541 (NRRL B-12401), AJ11542 (NRRL B-12402, British Patent No. 2075055), and 218 strain (VKPM B-8125, Russian Patent No. 2209248) and 73 strain (VKPM B-8126, Russian Patent No. 2215782) resistant to norleucine, which is an analogue of L-methionine. Furthermore, an L-methionine-producing bacterium, or a parent strain that can be used to construct such a bacterium also include AJ13425 (FERM P-16808, Japanese Patent Laid-open (Kokai) No. 2000-139471, U.S. Pat. No. 7,611,873) derived from the E. coli W3110. AJ13425 is an L-threonine auxotrophic strain deficient in the methionine repressor, in which intracellular S-adenosylmethionine synthetase activity is attenuated, and intracellular homoserine transsuccinylase activity, intracellular cystathionine γ-synthase activity, and intracellular aspartokinase-homoserine dehydrogenase II activity are enhanced. AJ13425 was deposited on May 14, 1998 at the National Institute of Bioscience and Human Technology, Agency of Industrial Science and Technology, Ministry of International Trade and Industry (currently National Institute of Advanced Industrial Science and Technology, International Patent Organism Depositary, Address: Tsukuba Central 6, 1-1, Higashi 1-Chome, Tsukuba-shi, Ibaraki-ken, 305-8566, Japan), and assigned an accession number of FERM P-16808.

Furthermore, an ability to produce any compounds biosynthesized by using L-methionine as a starting material, such as S-adenosylmethionine, can also be imparted or enhanced by increasing the activity of an enzyme of the biosynthesis system of the objective compound, or by reducing the activity of an enzyme of a pathway branching away from the biosynthesis pathway of the objective compound or an enzyme that decomposes the objective compound. For example, S-adenosylmethionine-producing ability can be imparted or enhanced by enhancing the methionine adenosyltransferase activity (European Patent Laid-open Nos. 0647712 and 1457569) or by enhancing the secretion factor MdfA (U.S. Pat. No. 7,410, 789).

Increasing the Activity of Protein Encoded by yeeE Gene

The bacterium as described herein can be obtained by modifying such a bacterium as mentioned above belonging to the family Enterobacteriaceae and having an ability to produce a sulfur-containing amino acid so that the activity of the protein encoded by the yeeE gene (henceforth also referred to as "YeeE" or "YeeE protein") is increased. Alternatively, this ability can also be imparted or enhanced after modifying a bacterium so that the activity of the YeeE protein is increased.

The expression "the activity of the protein encoded by the yeeE gene is increased" means that the activity of the protein encoded by the yeeE gene is increased compared with a non-modified strain such as a wild-type strain or a parent strain. Although the degree of increase of the activity of the protein is not particularly limited so long as the activity of the protein is increased as compared with a non-modified strain, the activity of the protein can be increased 1.5 times or more, 2 times or more, or even 3 times or more, as compared to that of a non-modified strain. Furthermore, the expression "the activity of the protein encoded by the yeeE gene increases" includes not only when the activity of the YeeE protein is increased in a strain intrinsically having the activity of the YeeE protein, but also when imparting the activity of the YeeE protein to a strain intrinsically deficient in the activity of the YeeE protein. That is, for example, this expression can include when imparting the activity of the YeeE protein to *Pantoea ananatis*, which is intrinsically deficient in the yeeE gene.

An example of a modification for increasing the activity of the YeeE protein is, for example, increasing the expression of the yeeE gene.

Another example of a modification for enhancing the expression of the yeeE gene is, for example, increasing the copy number of the yeeE gene in cells by using a gene recombination technique. For example, a recombinant DNA can be prepared by ligating a DNA fragment containing the yeeE gene with a vector that can function in a host bacterium, preferably a multi-copy type vector, and it can be introduced into the bacterium to transform it. Examples of such a vector include vectors autonomously replicable in host bacterium cells. Examples of vectors autonomously replicable in *Escherichia coli* cells include pUC19, pUC18, pHSG299, pHSG399, pHSG398, pACYC184 (pHSG and pACYC series vectors are available from Takara Bio), RSF1010, pBR322, pMW219 (pMW219 is available from NIPPON GENE), pSTV29 (available from Takara Bio), and so forth.

To introduce such a recombinant DNA into a bacterium, any known transformation methods that have hitherto been reported can be employed For example, the method of treating recipient cells with calcium chloride so as to increase the permeability thereof for DNA, which has been reported for *Escherichia coli* K-12 (Mandel, M. and Higa, A., J. Mol. Biol., 53, 159 (1970)), or the method of preparing competent cells from cells which are at the growth phase followed by introducing the DNA thereinto, which has been reported for *Bacillus subtilis* (Duncan, C. H., Wilson, G. A. and Young, F. E., Gene, 1, 153 (1977)), can be employed. In addition to these, the method of making DNA-recipient cells into protoplasts or spheroplasts, which can easily take up recombinant DNA, followed by introducing the recombinant DNA into the DNA recipient cells, which is known to be applicable to *Bacillus subtilis*, actinomycetes, and yeasts (Chang, S. and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci. USA, 75, 1929 (1978)), can also be applied.

Increasing the copy number of the yeeE gene can also be achieved by introducing multiple copies of the above-mentioned yeeE gene into the genomic DNA of a bacterium. Multiple copies of the yeeE gene can be introduced into the genomic DNA of a bacterium by homologous recombination using a sequence present on the genomic DNA in multiple copies as targets. As sequences present in the genomic DNA at multiple copies, repetitive DNAs, and inverted repeats existing at the ends of a transposon can be used. Another yeeE gene can be linked in tandem to the yeeE gene present on a genome, or it can be introduced so that it overlaps with an unnecessary gene on a genome. Such gene transfer can be attained by using a temperature sensitive vector or an integration vector.

Alternatively, as disclosed in Japanese Patent Laid-open (Kokai) No. 2-109985, it is also possible to incorporate the yeeE gene into a transposon, and transfer it so that multiple copies of the gene are introduced into the genomic DNA. Transfer of the gene onto the genome can be confirmed by performing Southern hybridization using a part of the yeeE gene as a probe.

Furthermore, in addition to the increasing the gene copy number, the expression of the yeeE gene can also be enhanced by replacing an expression control sequence such as a promoter of the yeeE gene on a genome DNA or plasmid with a stronger one, by making the −35 and −10 regions of the gene closer to the consensus sequence, by amplifying a regulator that increases the expression of the yeeE gene, or by deleting or attenuating a regulator that decreases the expression of the yeeE gene, according to the methods described in International Patent Publication WO00/18935. For example, the lac promoter, trp promoter, trc promoter, tic promoter, araBA promoter, PR and PL promoters of lambda phage, tet promoter, T7 promoter, Φ10 promoter, and so forth are known as strong promoters. Furthermore, the promoter of the threonine operon of *Escherichia coli* can also be used. The promoter or SD region of the yeeE gene can also be modified so as to become stronger by introducing a nucleotide substitution or the like. For example, the sequence of the SD region of the yeeE gene can be wholly replaced with the sequence of the SD region downstream from the Φ10 promoter. Examples of methods for evaluating the strength of a promoter and examples of strong promoters are described in the paper of Goldstein et al. (Prokaryotic promoters in biotechnology, Biotechnol. Annu. Rev., 1, 105-128 (1995)) and so forth. In addition, it is known that substitution of several nucleotides in the spacer between the ribosome binding site (RBS) and translation initiation codon, especially a sequence immediately upstream from the initiation codon, can greatly affect mRNA translation efficiency, and therefore it is also possible to modify this sequence to improve the translation efficiency. Expression control regions such as the promoter of the yeeE gene can also be identified by using a promoter probe vector or gene analysis software such as GENETYX. By such substitution or modification of promoter as described above, the expression of the yeeE gene can be enhanced. An expression control sequence can be replaced by, for example, a method using a temperature sensitive plasmid or Red-driven integration (WO2005/010175).

The expression amount of the yeeE gene can also be increased by, for example, modulating a control factor that positively or negatively controls the yeeE gene expression. Examples of the control factor include, for example, those belonging to the LysR family or the like, and they can be found by using the database EcoCyc (ecocyc.org) or the like. It is sufficient that transcription of the yeeE gene is increased, or that the amount of the YeeE protein is increased, by modulating the control factor.

An increase in the expression of the yeeE gene can be confirmed by confirming an increase in the transcription amount of the yeeE gene or an increase in the amount of the YeeE protein.

An increase in the transcription amount of the yeeE gene can be confirmed by comparing the amount of mRNA transcribed from the gene with that observed in a wild-type strain or a non-modified strain. Examples of the method for evaluating the amount of mRNA include Northern hybridization, RT-PCR, and so forth (Molecular Cloning, Cold Spring Harbor Laboratory Press, Cold Spring Harbor, USA, 2001). The amount of mRNA can be increased, for example, 1.5 times or more, 2 times or more, or 3 times or more, as compared with that of a non-modified strain.

An increase of the amount of the YeeE protein can be confirmed by Western blotting using an antibody (Molecular Cloning, Cold Spring Harbor Laboratory Press, Cold Spring Harbor (USA) (2001)). The amount of the protein can be increased by, for example, 1.5 times or more, 2 times or more, or 3 times or more, as compared with that of a non-modified strain.

logues of the gene. Examples of homologues of the gene can include genes that can be amplified by PCR using the chromosome of a microorganism such as bacteria belonging to the family Enterobacteriaceae and coryneform bacteria as a template and synthetic oligonucleotides prepared on the basis of, for example, the nucleotide sequence of SEQ ID NO: 13.

Examples of the yeeE gene homologues of bacteria other than *Escherichia coli* can include the yeeE genes isolated from the following bacteria (Table 1). In Table 1, Identity (%) indicates the identity determined by BLAST between the YeeE protein of the *Escherichia coli* K12 strain (SEQ ID NO: 14) and the homologue of each bacterium. The accession numbers are the accession numbers of the NCBI database.

TABLE 1

| Strain | Annotation | Identity % | Accession No. |
| --- | --- | --- | --- |
| *Escherichia fergusonii* ATCC 35469 | conserved hypothetical protein | 98 | YP_002383217 |
| *Shigella sonnei* Ss 046 | putative transport system permease protein | 98 | VP_310974 |
| *Shigella flexneri* 2a str. 301 | putative transport system permease protein | 97 | NP_707905 |
| *Shigella flexneri* 5 str. 8401 | putative transport system permease protein | 97 | VP_689505 |
| *Citrobacter rodentium* ICC168 | hypothetical protein | 89 | YP_003365700 |
| *Bacillus coagulans* 36D1 | protein of unknown function | 69 | ZP_04431645 |
| *Staphylococcus saprophyticus* subsp. *saprophyticus* ATCC 15305 | putative transporter component | 59 | YP_300924 |
| *Staphylococcus aureus* subsp. *aureus* MW2 | hypothetical protein | 57 | NP_646786 |
| *Staphylococcus epidermidis* M23864:W 1 | protein of hypothetical function | 57 | ZP_04817294 |
| *Staphylococcus lugdunensis* HKU09-01 | putative transport system permease protein | 56 | VP_003471236 |
| *Staphylococcus hominis* SK119 | inner membrane protein | 55 | ZP_04059216 |
| *Staphylococcus wameri* L37603 | inner membrane protein | 57 | ZP_04678741 |
| *Aggregatibacter aphrophilus* NJ8700 | inner membrane protein | 55 | YP_003007582 |
| *Macrococcus caseolyticus* JCSC5402 | hypothetical protein | 54 | YP_002559782 |
| *Actinobacillus minor* 202 | hypothetical protein | 55 | ZP_05629354 |
| *Streptococcus thermophilus* LMG 18311 | hypothetical protein | 53 | YP_140261 |
| *Helicobacter canadens* is MIT 98-5491 | inner membrane protein | 51 | ZP_03657109 |
| *Campylobacter jejuni* subsp. *doylei* 269.97 | inner membrane protein | 50 | YP_001399001 |
| *Bacillus tusciae* DSM 2912 | protein of unknown function | 52 | YP_003591000 |
| *Actinomyces* sp. *oral taxon* 848 str. F0332 | putative transport system permease protein | 51 | ZP_06162006 |

Furthermore, for the genes encoding SAT and the like as described above, a recombinant DNA can be introduced into a bacterium and the copy number of the gene can be increased, in a similar manner.

The yeeE gene of the *Escherichia coli* K12 MG1655 strain corresponds to a complementary sequence of the sequence at positions 2082491 to 2083549 in the genome sequence registered at the NCBI database as GenBank accession NC_000913 (VERSION NC_000913.2 GI: 49175990). The yeeE gene of the *Escherichia coli* K12 MG1655 strain is synonymous with ECK2007 or JW1995. Furthermore, the YeeE protein of the *Escherichia coli* K12 MG1655 strain is registered as GenBank accession NP_416517 (version NP_416517.1 GI: 16129954, locus_tag="b2013"). The nucleotide sequence of the yeeE gene of the MG1655 strain and the amino acid sequence encoded by this gene are shown as SEQ ID NOS: 13 and 14, respectively.

Because the nucleotide sequence of the yeeE gene can differ depending on the genus, species, or strain from which it is isolated, the yeeE gene to be modified so that the activity of the YeeE protein is increased can be a variant of the nucleotide sequence of SEQ ID NO: 13. A variant of the yeeE gene can be searched for by using BLAST (blast.genome.jp) or the like with referring to the nucleotide sequence of SEQ ID NO: 13. Furthermore, the variant of the yeeE gene can include homo- The yeeE gene can also be a gene coding for a protein having the amino acid sequence of the YeeE protein as mentioned above, but which can include substitution, deletion, insertion, addition, or the like of one or several amino acid residues at one or several positions, so long as it codes for a protein, which when the protein's activity is increased, improves sulfur-containing amino acid-producing ability as compared to an unmodified bacterium. Although the number meant by the term "one or several" can differ depending on positions of amino acid residues in the three-dimensional structure of the protein or types of amino acid residues, specifically, it can be 1 to 20, 1 to 10, or 1 to 5. The above substitution, deletion, insertion, or addition of one or several amino acid residues can be a conservative mutation that maintains the normal function of the protein. The conservative mutation is typically a conservative substitution. The conservative substitution is, for example, a mutation wherein substitution takes place mutually among Phe, Trp and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having hydroxyl group. Specific examples of substitutions considered as conservative substitutions include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The amino acid substitution, deletion, insertion, addition, inversion etc. can be a result of a naturally-occurring mutation (mutant or variant) due to an individual difference, a difference of species, or the like, of the bacterium from which the gene is derived.

Furthermore, the gene having such a conservative mutation as mentioned above can be a gene coding for a protein having a homology of 80% or more, 90% or more, 95% or more, 97% or more, or even 99% or more, to the total amino acid sequence of the YeeE protein, and wherein the increase of the intracellular activity of this protein improves the ability of the bacterium to produce sulfur-containing amino acid. In this specification, "homology" can mean "identity".

Furthermore, the yeeE gene can be a DNA that is able to hybridize with a probe that can be prepared from a known gene sequence, such as a complementary sequence of the nucleotide sequence of SEQ ID NO: 13, under stringent conditions, and codes for a protein having a function equivalent to that of the YeeE protein. The "stringent conditions" can refer to conditions under which a so-called specific hybrid is formed, and a non-specific hybrid is not formed. Examples of the stringent conditions include those under which highly homologous DNAs hybridize to each other, for example, DNAs not less than 80% homologous, not less than 90% homologous, not less than 95% homologous, not less than 97% homologous, or even not less than 99% homologous, hybridize to each other, and DNAs less homologous than the above do not hybridize to each other, or conditions of washing of typical Southern hybridization, i.e., washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe can be a part of the sequence complementary to the gene. Such a probe can be prepared by PCR using oligonucleotides prepared on the basis of a known gene sequence as primers and a DNA fragment containing the nucleotide sequence as a template. For example, when a DNA fragment having a length of about 300 bp is used as the probe, the washing conditions of the hybridization can be, for example, 50° C., 2×SSC and 0.1% SDS.

The aforementioned explanation of the variants of genes and proteins can also be similarly applied to enzymes such as serine acetyltransferase and 3-phosphoglycerate dehydrogenase and the YdeD protein, as well as the genes coding for them.

In the chromosome of *Escherichia coli*, the yeeD gene is present downstream from the yeeE gene, and it is thought that both genes form an operon (database "EcoCys", ecocyc.org; database "RegulonDB", regulondb.ccg.unam.mx). In general, genes forming an operon serve a common function or related functions in many cases. Therefore, when a modification for increasing the activity of the YeeE protein results in a certain effect, a modification for increasing the activity of the YeeD protein can result in a similar effect. The modification for increasing the activity of the YeeD protein can be effected together with the modification for increasing the activity of the YeeE protein.

<2> Method for Producing Sulfur-Containing Amino Acid, Related Substance Thereof, or Mixture Thereof By culturing the bacterium in accordance with the presently described subject matter in a medium and collecting a sulfur-containing amino acid, a related substance thereof, or a mixture of them from the medium, these compounds can be produced. When the sulfur-containing amino acid is L-cysteine, examples of the related substance of L-cysteine include S-sulfocysteine, thiazolidine derivatives, hemithioketals corresponding to the thiazolidine derivatives, and so forth. When the sulfur-containing amino acid is L-methionine, examples of the related substance of L-methionine include S-adenosylmethionine and so forth.

Examples of the medium that can be used include ordinary media containing a carbon source, nitrogen source, sulfur source, inorganic ions, and other organic components as required.

Examples of the carbon source include, for example, saccharides such as glucose, fructose, sucrose, molasses, and starch hydrolysate, and organic acids such as fumaric acid, citric acid, and succinic acid.

Examples of the nitrogen source include, for example, inorganic ammonium salts such as ammonium sulfate, ammonium chloride, and ammonium phosphate, organic nitrogen such as soybean hydrolysate, ammonia gas, and aqueous ammonia.

Examples of the sulfur source include, for example, inorganic sulfur compounds, such as sulfates, sulfites, sulfides, hyposulfites, and thiosulfates.

As organic trace amount nutrients, it is desirable to add required substances such as vitamin $B_1$, yeast extract, or the like in appropriate amounts. Other than these, potassium phosphate, magnesium sulfate, iron ions, manganese ions, and so forth are added in small amounts, as required.

The culture can be performed under aerobic conditions for 30 to 90 hours. The culture temperature can be controlled to 25° C. to 37° C., and pH can be controlled to be 5 to 8 during the culture. For pH adjustment, inorganic or organic acidic or alkaline substances, ammonia gas, and so forth can be used. The sulfur-containing amino acid from the culture broth can be collected by a combination of an ordinary ion exchange resin method, precipitation, and other known methods.

L-cysteine obtained as described above can be used for production of L-cysteine derivatives. Examples of the L-cysteine derivatives include methylcysteine, ethylcysteine, carbocisteine, sulfocysteine, acetylcysteine, and so forth.

Furthermore, when a thiazolidine derivative of L-cysteine accumulates in the medium, L-cysteine can be produced by collecting the thiazolidine derivative from the medium and breaking the reaction equilibrium between the thiazolidine derivative and L-cysteine so that L-cysteine is excessively produced Furthermore, when S-sulfocysteine accumulates in the medium, it can be converted into L-cysteine by reduction using a reducing agent such as dithiothreitol.

EXAMPLE

Hereafter, the present invention will be explained more specifically with reference to the following non-limiting example.

(1) Construction of L-Cysteine-Producing Bacterium

A single plasmid, pACYC-DES, carrying a mutant cysE coding for a mutant serine acetyltransferase which reduces feedback inhibition by L-cysteine (U.S. Patent Published Application No. 20050112731(A1)), the ydeD gene coding for an L-cysteine secretion factor (U.S. Pat. No. 5,972,663), and a mutant serA gene coding for a 3-phosphoglycerate dehydrogenase which reduces feedback inhibition by L-serine (U.S. Pat. No. 6,180,373), was introduced into the *Escherichia coli* MG1655 strain and the *Pantoea ananatis* SC17 strain, so as to construct L-cysteine-producing bacteria MG1655/pACYC-DES and SC17/pACYC-DES. In the mutant serine acetyltransferase, the threonine residue at position 167 was replaced with an alanine residue. Furthermore, in the 3-phosphoglycerate dehydrogenase, the tyrosine residue at position 410 was deleted. The construction of pACYC-DES is described in Japanese Patent Laid-open (Kokai) No. 2005-137369 (U.S. Patent Published Application No. 20050124049(A1), European Patent Laid-open No. 1528108 (A1)).

(2) Construction of Plasmid pMIV-Pnlp8-yeeE (Ec) for Expression of yeeE Gene

The plasmid pMIV-Pnlp8-yeeE (Ec) for overexpression of the yeeE gene, to be used for enhancing the activity of the YeeE protein, was constructed as follows.

(2-1) Construction of Plasmid pMIV-Pnlp0-YeaS3

The chromosomal DNA of the *Escherichia coli* MG1655 strain was used as a template, and P1 (agctgagtcgaccccccag-gaaaaattggttaataac, SEQ ID NO: 1) and P2 (agctgagcagcttc-caactgcgctaatgacgc, SEQ ID NO: 2) were used as primers, in PCR to obtain a DNA fragment containing the promoter region of the nlpD gene (Pnlp0) of about 300 bp. Recognition sites for the restriction enzymes SalI and PaeI were inserted at the 5' ends of each of these primers. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and the final cycle of 72° C. for 5 minutes. The obtained fragment was digested with SalI and PaeI, and inserted into pMIV-5J5 (Japanese Patent Laid-open (Kokai) No. 2008-99668) at the SalI-PaeI site, so as to obtain a plasmid pMIV-Pnlp0. The nucleotide sequence of the PaeI-SalI fragment of the Pnlp0 promoter inserted in this pMIV-Pnlp0 plasmid is as shown in SEQ ID NO: 3.

Then, the chromosomal DNA of the MG1655 strain was used as a template, and P3 (agctgatctagaaaacagaatttgcctg-gcggc, SEQ ID NO: 4) and P4 (agctgaggatccaggaagagtttgta-gaaacgc, SEQ ID NO: 5) were used as primers, in PCR to obtain a DNA fragment containing the terminator region of the rrnB gene of about 300 bp. Recognition sites for the restriction enzymes XbaI and BamHI were inserted at the 5' ends of each of these primers. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 59° C. for 20 seconds, and 72° C. for 15 seconds, and the final cycle of 72° C. for 5 minutes. The obtained fragment was treated with XbaI and BamHI, and inserted into pMIV-Pnlp0 at the XbaI-BamHI site, so as to obtain a plasmid pMIV-Pnlp0-ter.

Then, the chromosomal DNA of the MG1655 strain was used as a template, and P5 (agctgagtcgacgtgttcgct-gaatacggggt, SEQ ID NO: 6) and P6 (agctgatctagagaaagcat-caggattgcagc, SEQ ID NO: 7) were used as primers, in PCR to obtain a DNA fragment of about 700 bp containing the yeaS gene. Recognition sites for the restriction enzymes SalI and XbaI were inserted at the 5' ends of each of these primers. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 55° C. for 20 seconds, and 72° C. for 15 seconds, and the final cycle of 72° C. for 5 minutes. The obtained fragment was digested with SalI and XbaI, and inserted into pMIV-Pnlp0-ter at the SalI-XbaI site, so as to obtain a plasmid pMIV-Pnlp0-YeaS3. Thus, a yeaS expression unit that includes the nlpD promoter, the yeaS gene, and the rrnB terminator ligated in this order in the pMIV-5JS vector was constructed.

(2-2) Construction of Plasmid pMIV-Pnlp8-YeaS3

In order to modify the −10 region of the nlpD promoter to make it into a stronger promoter, the −10 region was randomized by the following method. The nlpD promoter region (FIG. 1) contains two regions presumed to function as promoters, and their −10 regions and −35 regions are shown as P1(−10) and P1(−35), and P2(−10) and P2(−35), respectively. The plasmid pMIV-Pnlp0 was used as a template, and P1 and P7 (atcgtgaagatcttttccagtgttnan-nagggtgccttgcacggtnatnangtcactgg, SEQ ID NO: 8) were used as primers, in PCR to obtain a DNA fragment in which the −10 region at the 3' end of the nlpD promoter (P1(−10)) was randomized. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and the final cycle of 72° C. for 5 minutes.

Similarly, the plasmid pMIV-Pnlp0 was used as a template, and P2 and P8 (tggaaaagatcttcannnnncgctgacctgcg, SEQ ID NO: 9) were used as primers, in PCR to obtain a DNA fragment in which the −10 region at the 5' end of the nlpD promoter (P2(−10)) was randomized. The PCR cycle was as follows: 95° C. for 3 minutes, followed by 2 cycles of 95° C. for 60 seconds, 50° C. for 30 seconds, and 72° C. for 40 seconds, 25 cycles of 94° C. for 20 seconds, 60° C. for 20 seconds, and 72° C. for 15 seconds, and the final cycle of 72° C. for 5 minutes.

The 3' end fragment and 5' end fragment obtained as above can be ligated via the BglII sites designed into the primers P7 and P8, to construct the full length of a nlpD promoter in which two −10 regions are randomized. Using this fragment as a template and P1 and P2 as primers, in PCR, a DNA fragment containing the full length of the modified nlpD promoter is obtained. The PCR cycle was as follows: 95° C. for 3 minutes, followed by 2 cycles of 95° C. for 60 seconds, 50° C. for 30 seconds, and 72° C. for 40 seconds, 12 cycles of 94° C. for 20 seconds, 60° C. for 20 seconds, and 72° C. for 15 seconds, and the final cycle of 72° C. for 5 minutes.

The amplified fragment was digested with the restriction enzymes SalI and PaeI, for which sites were designed in the 5' ends of the primers, and inserted into the plasmid pMIV-Pnlp0-YeaS3 similarly digested with SalI and PaeI, thereby to substitute the mutant Pnlp for the wild-type nlpD promoter region (Pnlp0) on the plasmid. From such plasmids, one having the promoter sequence shown in SEQ ID NO: 10 (Pnlp8) was selected, and designated pMIV-Pnlp8-YeaS7. The nucleotide sequence of the PaeI-SalI fragment of the Pnlp8 promoter inserted in this plasmid is shown in SEQ ID NO: 10. The Pnlp8 promoter is a stronger promoter compared with the Pnlp0 promoter.

(2-3) Construction of Plasmid pMIV-Pnlp8-yeeE (Ec) for Expression of yeeE Gene

By replacing the yeaS gene incorporated into the aforementioned expression plasmid pMIV-Pnlp8-YeaS7 with the yeeE gene, a plasmid carrying a yeeE expression unit, which includes the Pnlp8 promoter, the yeeE gene, and the rrnB terminator in this order in the pMIV-5JS vector, was constructed. The construction method of the plasmid pMIV-Pnlp8-yeeE (Ec) for overexpression of the yeeE gene is shown below.

The genomic DNA of the MG1655 strain was used as a template, and yeeE(Ec)SalI-F (acgcgtcgacatgttttcaatgatattaagcgggc, SEQ ID NO: 11) and yeeE(Ec)XbaI-R (ctagtctagattaatttgccgcagcagttgcc, SEQ ID NO: 12) were used as primers, in PCR with a cycle of 94° C. for 5 minutes, followed by 30 cycles of 98° C. for 5 seconds, 55° C. for 5 seconds, and 72° C. for 90 seconds, and keeping at 4° C. for the final cycle, to obtain the amplified yeeE gene of *Escherichia*. At the both ends of the primers, SalI and XbaI sites were inserted. The amplified fragment was digested with SalI and XbaI, and inserted into pMIV-Pnlp8-YeaS7 similarly digested with SalI and XbaI to construct a plasmid pMIV-Pnlp8-yeeE (Ec). As a corresponding empty vector (for control), pMIV-5JS (Japanese Patent Laid-open (Kokai) No. 2008-99668) was used. The DNA sequence of the yeeE gene is shown as SEQ ID NO: 13, and the predicted amino acid sequence of the yeeE gene product is shown as SEQ ID NO: 14.

(3) L-Cysteine Production Culture (*Escherichia coli*)

In order to investigate the effect of overexpression of the yeeE gene on the fermentative production of L-cysteine and L-cysteine related compounds, culture for the fermentative production was performed with strains obtained by introducing the yeeE overexpression plasmid pMIV-Pnlp8-yeeE (Ec) and the empty vector pMIV-5JS for the control into the aforementioned L-cysteine-producing *Escherichia coli* MG1655/pACYC-DES, and the production amounts of L-cysteine and L-cysteine-related compounds were compared. For the culture, a cysteine production medium having the following composition was used.

L-cysteine production medium (concentrations of the components are final concentrations):

| Components 1: | |
| --- | --- |
| a. $(NH_4)_2SO_4$ | 15 g/L |
| b. $KH_2PO_4$ | 1.5 g/L |
| c. $MgSO_4 \cdot 7H_2O$ | 1 g/L |
| d. Tryptone | 10 g/L |
| e. Yeast extract | 5 g/L |
| f. NaCl | 10 g/L |
| g. L-Histidine hydrochloride monohydrate | 135 mg/L |
| h. L-Methionine | 300 mg/L |
| Component 2: | |
| a. Glucose | 40 g/L |
| Component 3: | |
| a. Sodium thiosulfate | 7 g/L |
| Component 4: | |
| a. Pyridoxine hydrochloride | 2 mg/L |
| Component 5: | |
| a. Calcium carbonate | 20 g/L |

For the components, stock solutions of 100/47.5-fold concentration (Components 1), 100/47.5-fold concentration (Components 2), 50-fold concentration (Components 3), and 1000-fold concentration (Component 4) were prepared. The stock solutions were mixed at the time of use, and the defined volume was obtained with sterilized water to attain the final concentrations. Sterilization was performed by autoclaving at 110° C. for 30 minutes (Components 1 and 2), dry heat sterilization at 180° C. for 5 hours or longer (Component 5), or filter sterilization (Components 3 and 4).

The L-cysteine production culture was performed as follows. Each L-cysteine-producing strain was spread on LB agar medium, and pre-culture was performed overnight at 37° C. Then, cells corresponding to about 7 cm on the plate were scraped with an inoculation loop of 10-µl size (NUNC Blue Loop) three times (three loops), and inoculated into 2 ml of the aforementioned L-cysteine production medium contained in a large test tube (internal diameter: 23 mm, length: 20 cm) to adjust the cell amount for each test tube at the time of the start of the culture so that it is substantially the same. Culture was performed at 32° C. with shaking, and terminated after 30 hours. L-cysteine and L-cysteine-related compounds such as cystine were produced in the medium and quantified by the method described by Gaitonde, M. K. (Biochem. J., August 1967, 104(2):627-33). The experiment was performed in quadruplicate for each strain, and the produced L-cysteine amounts (averages) and standard deviations, and L-cysteine yields based on the consumed glucose are shown in Table 2. The accumulated L-cysteine concentration is increased by overexpression of the yeeE gene. Therefore, L-cysteine production can be improved by increasing the activity of the YeeE protein.

TABLE 2

Effect of overexpression of yeeE gene on L-cysteine production in *Escherichia coli*

| Plasmid | L-cysteine (g/L) | Yield based on consumed saccharide (%) |
| --- | --- | --- |
| pMIV-5JS | 0.65 ± 0.04 | 1.95 |
| pMIV-Pnlp8-yeeE(Ec) | 1.86 ± 0.06 | 4.65 |

(4) L-cysteine Production Culture (*Pantoea ananatis*)

In order to investigate the effect of overexpression of the yeeE gene on the fermentative production of L-cysteine and L-cysteine-related compounds, culture for the fermentative production was performed with strains obtained by introducing the yeeE overexpression plasmid pMIV-Pnlp8-yeeE (Ec) and the empty vector pMIV-5JS for the control into the aforementioned L-cysteine-producing *Pantoea ananatis* SC17/pACYC-DES, and the production amounts of L-cysteine and L-cysteine-related compounds were compared. The methods for the L-cysteine production culture and quantification of L-cysteine were substantially the same as those used in the aforementioned example using *Escherichia coli*, except that the inoculation amount was changed to one loop, and the culture time was changed to 22 hours. The experiment was performed in quadruplicate for each strain, and the produced L-cysteine amounts (averages) and standard deviations, and L-cysteine yields based on the consumed glucose are shown in Table 3. The accumulated L-cysteine concentration is increased by overexpression of the yeeE gene. Therefore, L-cysteine production can be improved by increasing the activity of the YeeE protein.

TABLE 3

Effect of overexpression of yeeE gene on L-cysteine production in *Pantoea ananatis*

| Plasmid | L-cysteine (g/L) | Yield based on consumed saccharide (%) |
| --- | --- | --- |
| pMIV-5JS | 0.27 ± 0.04 | 0.67 |
| pMIV-Pnlp8-yeeE(Ec) | 0.41 ± 0.04 | 1.03 |

Industrial Applicability

According to the present invention, the sulfur-containing amino acid-producing ability of a bacterium can be improved, and a sulfur-containing amino acid, a related substance thereof, or a mixture of them can be efficiently produced.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

Explanation of Sequence Listing

SEQ ID NO: 1, primer for amplification of Pnlp0
SEQ ID NO: 2, primer for amplification of Pnlp0
SEQ ID NO: 3, nucleotide sequence of Pnlp0
SEQ ID NO: 4, primer for amplification of terminator region of rrnB gene
SEQ ID NO: 5, primer for amplification of terminator region of rrnB gene
SEQ ID NO: 6, primer for amplification of yeaS gene
SEQ ID NO: 7, primer for amplification of yeaS gene
SEQ ID NO: 8, primer for randomization of −10 region of Pnlp0 (3' end side)
SEQ ID NO: 9, primer for randomization of −10 region of Pnlp0 (5' end side)
SEQ ID NO: 10, nucleotide sequence of Pnlp8
SEQ ID NO: 11, primer for amplification of yeeE gene
SEQ ID NO: 12, primer for amplification of yeeE gene
SEQ ID NO: 13, nucleotide sequence of wild-type *Escherichia coli* yeeE gene
SEQ ID NO: 14, amino acid sequence of wild-type *Escherichia coli* YeeE protein
SEQ ID NO: 15, nucleotide sequence of Pnlp0 including ligation site with yeaS gene
SEQ ID NO: 16, nucleotide sequence of Pnlp8 including ligation site with yeaS gene

The invention claimed is:

1. A method for producing a sulfur-containing amino acid, a related substance thereof, or a mixture thereof, which comprises:
culturing the bacterium belonging to the family Enterobacteriaceae, which has a sulfur-containing amino acid-producing ability and is modified so that the expression amount of the YeeE gene is increased, in a medium; and
collecting a sulfur-containing amino acid, a related substance thereof, or a mixture thereof from the medium,
wherein said expression amount of the yeeE gene is increased by a method selected from the group consisting of:
a) increasing the copy number of the yeeE gene,
b) modifying an expression control sequence of the gene, and
c) combinations thereof, and
wherein said yeeE gene encodes a protein selected from the group consisting of:
(A) a protein comprising the amino acid sequence of SEQ ID NO: 14, and
(B) a protein comprising the amino acid sequence of SEQ ID NO: 14, but which includes 1 to 10 amino acid substitutions, deletions, insertions, or additions, and wherein the increase in said protein's activity improves the ability of said bacterium to produce a sulfur-containing amino acid, and
(C) a protein comprising an amino acid sequence having a homology of 90% or more to SEQ ID NO: 14.

2. The method according to claim 1, wherein said sulfur-containing amino acid is L-cysteine.

3. The method according to claim 1, wherein said sulfur-containing amino acid is L-cysteine, and said related substance thereof is cystine or a thiazolidine derivative.

4. The method according to claim 1, wherein said yeeE gene comprises a DNA selected from the group consisting of:
(a) a DNA comprising the nucleotide sequence of SEQ ID NO: 13, and
(b) a DNA which is able to hybridize with a sequence complementary to the nucleotide sequence of SEQ ID NO: 13 under stringent conditions comprising washing at a salt concentration and temperature corresponding to 0.1×SSC, 0.1% SDS at 60° C., and said DNA encodes a protein which improves the ability of said bacterium to produce a sulfur-containing amino acid when the activity of said protein is increased in said bacterium.

5. The method according to claim 1, wherein said bacterium further has at least one of the following characteristics:
i) increased serine acetyltransferase activity by a method selected from the group consisting of transforming the bacterium with a serine acetyltransferase gene, increasing the expression of a gene encoding serine acetyltransferase and combinations thereof,
ii) increased expression of the ydeD gene from *Escherichia coli*, and
iii) increased 3-phosphoglycerate dehydrogenase activity by a method selected from the group consisting of transforming the bacterium with a 3-phosphoglycerate dehydrogenase gene, increasing the expression of a gene encoding 3-phosphoglycerate dehydrogenase, and combinations thereof,
wherein said expression of the gene(s) is/are increased by a method selected from the group consisting of:
a) increasing the copy number of the gene(s),
b) modifying an expression control sequence of the gene (s), and
c) combinations thereof.

6. The method according to claim 1, wherein said bacterium is an *Escherichia* bacterium.

7. The method according to claim 6, wherein said bacterium is *Escherichia coli*.

8. The method according to claim 1, wherein said bacterium is a *Pantoea* bacterium.

9. The method according to claim 8, wherein said bacterium is *Pantoea ananatis*.

* * * * *

SEQUENCE LISTING

```
<160> NUMBER OF SEQ ID NOS: 16

<210> SEQ ID NO 1
<211> LENGTH: 36
<212> TYPE: DNA
<213> ORGANISM: Artificial Sequence
<220> FEATURE:
<223> OTHER INFORMATION: primer P1

<400> SEQUENCE: 1
agctgagtcg acccccagga aaaattggtt aataac                        36

<210> SEQ ID NO 2
<211> LENGTH: 33
<212> TYPE: DNA
<213> ORGANISM: Artificial Sequence
<220> FEATURE:
<223> OTHER INFORMATION: primer P2

<400> SEQUENCE: 2
agctgagcat gcttccaact gcgctaatga cgc                           33

<210> SEQ ID NO 3
<211> LENGTH: 313
<212> TYPE: DNA
<213> ORGANISM: Escherichia coli

<400> SEQUENCE: 3
gcatgcttcc aactgcgcta atgacgcagc tggacgaagg cgggattctc gtcttacccg     60
taggggagga gcaccagtat ttgaaacggg tgcgtcgtcg gggaggcgaa tttattatcg    120
ataccgtgga ggccgtgcgc tttgtccctt tagtgaaggg tgagctggct taaaacgtga    180
ggaaatacct ggatttttcc tggttatttt gccgcaggtc agcgtatcgt gaacatcttt    240
tccagtgttc agtagggtgc cttgcacggt aattatgtca ctggttatta accaatttt     300 cctgggggtc gac                                                      313

<210> SEQ ID NO 4
<211> LENGTH: 33
<212> TYPE: DNA
<213> ORGANISM: Artificial Sequence
<220> FEATURE:
<223> OTHER INFORMATION: primer P3

<400> SEQUENCE: 4
agctgatcta gaaaacagaa tttgcctggc ggc                           33

<210> SEQ ID NO 5
```

```
<211> LENGTH: 33
<212> TYPE: DNA
<213> ORGANISM: Artificial Sequence
<220> FEATURE:
<223> OTHER INFORMATION: primer P4

<400> SEQUENCE: 5
agctgaggat ccaggaagag tttgtagaaa cgc                           33

<210> SEQ ID NO 6
<211> LENGTH: 32
<212> TYPE: DNA
<213> ORGANISM: Artificial Sequence
<220> FEATURE:
<223> OTHER INFORMATION: primer P5

<400> SEQUENCE: 6
agctgagtcg acgtgttcgc tgaatacggg gt                            32

<210> SEQ ID NO 7
<211> LENGTH: 32
<212> TYPE: DNA
<213> ORGANISM: Artificial Sequence
<220> FEATURE:
<223> OTHER INFORMATION: primer P6

<400> SEQUENCE: 7
agctgatcta gagaaagcat caggattgca gc                            32

<210> SEQ ID NO 8
<211> LENGTH: 59
<212> TYPE: DNA
<213> ORGANISM: Artificial Sequence
<220> FEATURE:
<223> OTHER INFORMATION: primer P7
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t

<400> SEQUENCE: 8
atcgtgaaga tcttttccag tgttnannag ggtgccttgc acggtnatna ngtcactgg    59

<210> SEQ ID NO 9
<211> LENGTH: 32
<212> TYPE: DNA
<213> ORGANISM: Artificial Sequence
<220> FEATURE:
<223> OTHER INFORMATION: primer P8
<220> FEATURE:
<221> NAME/KEY: misc_feature
<222> LOCATION: (16)..(20)
<223> OTHER INFORMATION: n is a, t, g, or c

<400> SEQUENCE: 9
```

```
tggaaaagat cttcannnnn cgctgacctg cg                                    32

<210> SEQ ID NO 10
<211> LENGTH: 312
<212> TYPE: DNA
<213> ORGANISM: Artificial Sequence
<220> FEATURE:
<223> OTHER INFORMATION: Pnlp8

<400> SEQUENCE: 10
gcatgcttcc aactgcgcta atgacgcagc tggacgaagg cgggattctc gtcttacccg      60
taggggagga gcaccagtat ttgaaacggg tgcgtcgtcg gggaggcgaa tttattatcg     120
ataccgtgga ggccgtgcgc tttgtccctt tagtgaaggg tgagctggct aaaacgtga     180 ggaaatacct ggattttcc tggttatttt gccgcaggtc agcgtataat gaagatcttt     240
tccagtgttg acaagggtcc ttgcacggtt ataatgtcac tggttattaa ccaatttttc    300 ctggggtcg ac                                                          312

<210> SEQ ID NO 11
<211> LENGTH: 35
<212> TYPE: DNA
<213> ORGANISM: Artificial Sequence
<220> FEATURE:
<223> OTHER INFORMATION: primer yeeE(Ec)SalI-F

<400> SEQUENCE: 11
acgcgtcgac atgttttcaa tgatattaag cgggc                                 35

<210> SEQ ID NO 12
<211> LENGTH: 32
<212> TYPE: DNA
<213> ORGANISM: Artificial Sequence
<220> FEATURE:
<223> OTHER INFORMATION: primer yeeE(Ec)XbaI-R

<400> SEQUENCE: 12
ctagtctaga ttaatttgcc gcagcagttg cc                                    32

<210> SEQ ID NO 13
<211> LENGTH: 1059
<212> TYPE: DNA
<213> ORGANISM: Escherichia coli
<220> FEATURE:
<221> NAME/KEY: CDS
<222> LOCATION: (1)..(1059)

<400> SEQUENCE: 13 atg ttt tca atg ata tta agc ggg cta att tgt ggt gct ctg ctg gga       48
Met Phe Ser Met Ile Leu Ser Gly Leu Ile Cys Gly Ala Leu Leu Gly
1               5                   10                  15 ttt gtc atg cag cgt ggg cgt ttt tgc ctg aca ggt ggt ttt cgc gat       96
Phe Val Met Gln Arg Gly Arg Phe Cys Leu Thr Gly Gly Phe Arg Asp
                20                  25                  30 atg tat atc gtg aaa aat aat cgc atg ttt tac gcc ttg ctg att gca      144
Met Tyr Ile Val Lys Asn Asn Arg Met Phe Tyr Ala Leu Leu Ile Ala
            35                  40                  45 att tcg gta caa agc gtg ggg gtt ttt gcg tta att cag gcg ggc cta      192
Ile Ser Val Gln Ser Val Gly Val Phe Ala Leu Ile Gln Ala Gly Leu
        50                  55                  60 ctg act tac gaa gcc ggg gcg ttc ccg tgg ctt ggt act gtt ata ggt      240
Leu Thr Tyr Glu Ala Gly Ala Phe Pro Trp Leu Gly Thr Val Ile Gly
65                  70                  75                  80
```

```
ggg tat atc ttc ggg ctg gga att gtt ctg gcg ggt gga tgt gcc acc    288
Gly Tyr Ile Phe Gly Leu Gly Ile Val Leu Ala Gly Gly Cys Ala Thr
                85                  90                  95 ggg acc tgg tat cgc gcg ggt gag gga ttg atc ggc agt tgg atc gcg    336
Gly Thr Trp Tyr Arg Ala Gly Glu Gly Leu Ile Gly Ser Trp Ile Ala
            100                 105                 110 ctt ttc act tat atg gtg atg agt gcg gtg atg cgt tct cca cat gcc    384
Leu Phe Thr Tyr Met Val Met Ser Ala Val Met Arg Ser Pro His Ala
        115                 120                 125 agt ggt tta aat caa acc ttg cag cac tac agt act gaa cat aac tct    432
Ser Gly Leu Asn Gln Thr Leu Gln His Tyr Ser Thr Glu His Asn Ser
    130                 135                 140 att gct gag act ttt aat ttg tct gtg tgg ccg ttg gtt gcc gtt ttg    480
Ile Ala Glu Thr Phe Asn Leu Ser Val Trp Pro Leu Val Ala Val Leu
145                 150                 155                 160 ctg gtg ata acg ctc tgg gtg gtg atg aaa gag ttg aag aag cca aaa    528
Leu Val Ile Thr Leu Trp Val Val Met Lys Glu Leu Lys Lys Pro Lys
                165                 170                 175 ctc aaa gtc gcg acc tta ccg ccg cgc cga acc ggg atc gct cat att    576
Leu Lys Val Ala Thr Leu Pro Pro Arg Arg Thr Gly Ile Ala His Ile
            180                 185                 190 ctg ttt gaa aaa cgc tgg cat ccc ttt gtc aca gct gta ctc atc ggt    624
Leu Phe Glu Lys Arg Trp His Pro Phe Val Thr Ala Val Leu Ile Gly
        195                 200                 205 ttg att gcg ctt tta gcc tgg ccc ctg agt gaa gca acc gga cgc atg    672
Leu Ile Ala Leu Leu Ala Trp Pro Leu Ser Glu Ala Thr Gly Arg Met
    210                 215                 220 ttt ggg tta gga atc act tcc cca acg gcc aat att ctg caa ttt ctg    720
Phe Gly Leu Gly Ile Thr Ser Pro Thr Ala Asn Ile Leu Gln Phe Leu
225                 230                 235                 240 gtc gcg ggt gac atg aaa tac att aac tgg ggc gtt ttc ctg gtg tta    768
Val Ala Gly Asp Met Lys Tyr Ile Asn Trp Gly Val Phe Leu Val Leu
                245                 250                 255 ggg atc ttc gtg ggg tca ttt att gca gcc aaa gcg agc cgt gag ttc    816
Gly Ile Phe Val Gly Ser Phe Ile Ala Ala Lys Ala Ser Arg Glu Phe
            260                 265                 270 cgc gtt cgc gca gct gat gca caa aca aca tta cgt agc ggg tta ggt    864
Arg Val Arg Ala Ala Asp Ala Gln Thr Thr Leu Arg Ser Gly Leu Gly
        275                 280                 285 ggt gta ctg atg ggc ttc ggt gcc agt att gca ggt ggt tgc tct atc    912
Gly Val Leu Met Gly Phe Gly Ala Ser Ile Ala Gly Gly Cys Ser Ile
    290                 295                 300 ggt aat gga ctg gtt atg act gca atg acc tgg cag ggc tgg att    960
Gly Asn Gly Leu Val Met Thr Ala Met Met Thr Trp Gln Gly Trp Ile
305                 310                 315                 320 ggc ctt gta ttt atg att ctc gga gtc tgg act gcg tcc tgg ctt gtg   1008
Gly Leu Val Phe Met Ile Leu Gly Val Trp Thr Ala Ser Trp Leu Val
                325                 330                 335 tat gtt cga ccg cag cgt aag gcg cga ctg gca act gct gcg gca aat   1056
Tyr Val Arg Pro Gln Arg Lys Ala Arg Leu Ala Thr Ala Ala Ala Asn
            340                 345                 350 taa                                                                1059
```

<210> SEQ ID NO 14
<211> LENGTH: 352
<212> TYPE: PRT
<213> ORGANISM: Escherichia coli

<400> SEQUENCE: 14

| | | | | | | | | | | | | | | |
|---|---|---|---|---|---|---|---|---|---|---|---|---|---|---|
|Met|Phe|Ser|Met|Ile|Leu|Ser|Gly|Leu|Ile|Cys|Gly|Ala|Leu|Leu|Gly|
|1| | | |5| | | |10| | | |15| | |

Phe Val Met Gln Arg Gly Arg Phe Cys Leu Thr Gly Gly Phe Arg Asp
            20                      25                      30

Met Tyr Ile Val Lys Asn Asn Arg Met Phe Tyr Ala Leu Leu Ile Ala
            35                      40                      45

Ile Ser Val Gln Ser Val Gly Val Phe Ala Leu Ile Gln Ala Gly Leu
 50                      55                      60

Leu Thr Tyr Glu Ala Gly Ala Phe Pro Trp Leu Gly Thr Val Ile Gly
 65                      70                      75                      80

Gly Tyr Ile Phe Gly Leu Gly Ile Val Leu Ala Gly Gly Cys Ala Thr
            85                      90                      95

Gly Thr Trp Tyr Arg Ala Gly Glu Gly Leu Ile Gly Ser Trp Ile Ala
            100                     105                     110

Leu Phe Thr Tyr Met Val Met Ser Ala Val Met Arg Ser Pro His Ala
            115                     120                     125

Ser Gly Leu Asn Gln Thr Leu Gln His Tyr Ser Thr Glu His Asn Ser
 130                     135                     140

Ile Ala Glu Thr Phe Asn Leu Ser Val Trp Pro Leu Val Ala Val Leu
145                     150                     155                     160

Leu Val Ile Thr Leu Trp Val Val Met Lys Glu Leu Lys Lys Pro Lys
            165                     170                     175

Leu Lys Val Ala Thr Leu Pro Pro Arg Arg Thr Gly Ile Ala His Ile
            180                     185                     190

Leu Phe Glu Lys Arg Trp His Pro Phe Val Thr Ala Val Leu Ile Gly
            195                     200                     205

Leu Ile Ala Leu Leu Ala Trp Pro Leu Ser Glu Ala Thr Gly Arg Met
 210                     215                     220

Phe Gly Leu Gly Ile Thr Ser Pro Thr Ala Asn Ile Leu Gln Phe Leu
225                     230                     235                     240

Val Ala Gly Asp Met Lys Tyr Ile Asn Trp Gly Val Phe Leu Val Leu
            245                     250                     255

Gly Ile Phe Val Gly Ser Phe Ile Ala Ala Lys Ala Ser Arg Glu Phe
            260                     265                     270

Arg Val Arg Ala Ala Asp Ala Gln Thr Thr Leu Arg Ser Gly Leu Gly
            275                     280                     285

Gly Val Leu Met Gly Phe Gly Ala Ser Ile Ala Gly Gly Cys Ser Ile
            290                     295                     300

Gly Asn Gly Leu Val Met Thr Ala Met Met Thr Trp Gln Gly Trp Ile
305                     310                     315                     320

Gly Leu Val Phe Met Ile Leu Gly Val Trp Thr Ala Ser Trp Leu Val
            325                     330                     335

Tyr Val Arg Pro Gln Arg Lys Ala Arg Leu Ala Thr Ala Ala Ala Asn
            340                     345                     350

<210> SEQ ID NO 15
<211> LENGTH: 144
<212> TYPE: DNA
<213> ORGANISM: Escherichia coli

<400> SEQUENCE: 15
aaaacgtgag gaaataccctg gatttttcct ggttattttg ccgcaggtca gcgtatcgtg    60
aacatctttt ccagtgttca gtagggtgcc ttgcacggta attatgtcac tggttattaa   120 ccaattttc ctgggggata aatg                                          144

```
<210> SEQ ID NO 16
<211> LENGTH: 144
<212> TYPE: DNA
<213> ORGANISM: Artificial Sequence
<220> FEATURE:
<223> OTHER INFORMATION: Pnlp8

<400> SEQUENCE: 16
aaaacgtgag gaaatacctg gatttttcct ggttattttg ccgcaggtca gcgtataatg      60
aagatctttt ccagtgttga caagggtgcc ttgcacggtt ataatgtcac tggttattaa     120 ccaattttc ctgggggata aatg                                             144
```